(12) United States Patent
Moore

(10) Patent No.: US 6,225,258 B1
(45) Date of Patent: May 1, 2001

(54) CONTROLLED RELEASE PESTICIDE AND FERTILIZER BRIQUETTES

(75) Inventor: William P. Moore, Hopewell, VA (US)

(73) Assignee: Lesco Technologies LLC, Strongsville, OH (US)

( * ) Notice: Subject to any disclaimer, the term of this patent is extended or adjusted under 35 U.S.C. 154(b) by 0 days.

(21) Appl. No.: 09/344,083

(22) Filed: Jun. 25, 1999

(51) Int. Cl.$^7$ .............. A01N 25/08; C05G 3/02
(52) U.S. Cl. .................. 504/101; 504/360
(58) Field of Search .................. 504/360, 101

(56) References Cited

U.S. PATENT DOCUMENTS

| | | | |
|---|---|---|---|
| 2,991,170 | * 7/1961 | Szepesi et al. | 71/61 |
| 3,024,098 | 3/1962 | Austin et al. | 71/29 |
| 3,062,637 | 11/1962 | Marples et al. | 71/24 |
| 3,190,741 | * 6/1965 | Brandeis et al. | 71/28 |
| 3,647,416 | 3/1972 | Messman | 71/29 |
| 3,925,053 | 12/1975 | Kealy | 71/29 |
| 4,539,038 | * 9/1985 | Gombert | 71/64.11 |
| 5,174,804 | 12/1992 | Rehberg et al. | 71/3 |

OTHER PUBLICATIONS

Humate International. Information Bulletin. Feb. 1998.*
Humate International. Information Bulletin. Mar. 1999.*

* cited by examiner

Primary Examiner—S. Mark Clardy
(74) Attorney, Agent, or Firm—Arter & Hadden LLP

(57) ABSTRACT

An attrition and shatter resistant plant nutrient/pesticide briquette composition which slowly releases the nutrients and biologically active materials over long periods of time, comprising slow release plant nutrient particles, pesticide sorption particles, liquid systemic pesticide sorbed on the pesticide sorption particles to reduce pesticide leachability, an adhesive, coating the slow release plant nutrient and pesticide sorption particles, the composition formed into briquettes by pressing into dies at elevated pressures and temperatures to make briquettes resistant to attrition and shattering. A six step method is provided for the preparation of the slow releasing briquettes from slow release fertilizers, such as magnesium ammonium phosphate; pesticide sorption particles, such as activated carbon; liquid systemic pesticides emulsions, such as imidachloprid fosetyl-Al, and metalaxyl; and adhesives, such as a vinylidine chloride, 2-ethylhexyl acrylate, acrylic acid resin emulsion.

19 Claims, No Drawings

CONTROLLED RELEASE PESTICIDE AND FERTILIZER BRIQUETTES

FIELD OF THE INVENTION

This invention relates to the fields of pesticides and plant nutrients, and more particularly to pesticides and plant nutrients, combined into briquettes; the pesticides and plant nutrients exhibiting separately controllable releases throughout long periods of time. The new pesticide and plant nutrient composition comprises controlled release plant nutrient particles, and pesticides sorbed on particulate sorption solids, combined in the form of attrition and fracture resistant briquettes. The sorptive solids on which the pesticides are sorbed exhibit the ability to substantially reduce the leachability of the pesticide. The term pesticide is used herein to mean any, and all, biologically active chemicals used to beneficially treat plants, including insecticides, herbicides, algaecides, fungicides, and acaricides. The term sorb is used herein to mean absorb and/or adsorb. Typical plant nutrients of this invention are magnesium ammonium phosphate, magnesium potassium phosphate, ureaformaldehyde polymer and alkylidene diurea compounds. Typical sorption solids of this invention comprise: iron humate, silica gel, ground vegetable seed hulls, starch, wood flour, lignin, activated carbon, and paper waste.

BACKGROUND OF THE INVENTION

The prior art has provided several slow release fertilizers which work by occluding soluble fertilizer materials within agglomerates bound together by water insoluble binders. For example nitrogen, phosphorus, potassium and micronutrients may be bound together with ureaformaldehyde resins, or as in the case of U.S. Pat. No. 3,925,053 calcium sulfate hemihydrate may be used as a binder.

U.S. Pat. No. 3,647,416 discloses that bonded fertilizers may be produced in the form of a briquette using ureaformaldehyde resin as the binder. U.S. Pat. No. 3,024,098 also discloses a ureaformaldehyde based fertilizer which is prepared by compressing into agglomerates to provide briquettes or spikes with high resistances to crushing.

Compressed briquettes have also been prepared with improved nitrogen release when isobutylidiene diurea was the main source of nitrogen.

There has been less information in the prior art regarding controlled release of pesticides than of plant nutrients. There has been some success reported in controlling pesticide release rates when granular pesticides were coated or encapsulated with water insoluble plastics such as polyvinylchloride as in U.S. Pat. No. 3,062,637.

In U.S. Pat. No. 5,174,804 a fertilizer/pesticide composition was disclosed which included a fertilizer and a pesticide admixed with a binder to form a briquette in which the fertilizer occludes the pesticide, with the briquette essentially free of water soluble materials. This briquette when placed in the soil releases nutrients and pesticides into the soil over an extended period of time.

Although U.S. Pat. No. 5,174,804 advanced the art of controlled release plant nutrients and pesticides, it did not provide a method for separate control of the release of the pesticides and the plant nutrients. It also does not provide for wide variations in the amounts of pesticide or plant nutrient materials in a briquette product.

OBJECTS OF THE INVENTION

It is an object of this invention to provide an improved plant nutrient/pesticide briquette composition which releases pesticide and plant nutrients throughout a long period of time.

It is another object of this invention to provide an improved plant nutrient/pesticide briquette composition which provides plant nutrients and pesticides, the releases of which are separately controllable.

It is a further object of this invention to provide an improved plant nutrient/pesticide briquette composition wherein liquid pesticide is sorbed on, or in, a particulate filler to control the leaching of the pesticide from the briquette for longer periods of time.

It is a further object of this invention to provide a plant nutrient/pesticide briquette which exhibits improved physical integrity, using pesticide sorbed on pesticide sorption solids, which are coated on plant food granules by means of a thermoplastic adhesive.

It is a further object of this invention to provide an improved method for preparing plant nutrient/pesticide briquettes, requiring small amounts of thermoplastic adhesive.

SUMMARY OF THE INVENTION

To attain the aforementioned objects and to improve existing fertilizer/pesticide compositions of the prior art, I have discovered a composition which slowly releases both pesticides (biologically active materials) and plant nutrients throughout a long period of time. This new composition is particularly effective because a liquid biologically active material is sorbed on pesticide sorption particles which have the ability to sorb pesticides and reduce their leachability. The pesticide sorption particles and particles of slow release plant nutrients are coated with a small amount of adhesive, and then compressed to form attrition and shatter resistant briquettes. Surprisingly, the briquettes release both the liquid pesticide and the plant nutrients at slow rates, and the release rates of the biologically active materials may be independently varied by changes in the amount of, and properties of, the pesticide sorption particles, and by the amount of pesticide sorbed thereon. The slow release properties of the plant nutrients and the pesticides may be changed by variations in the amount of adhesive used in coating the slow release nutrient granules, and the pesticide sorption particles prior to briquetting, and by the conditions under which the nutrient granules and the sorption particles are bound together into attrition and shatter resistant briquettes. The method of combination, and the amounts of the ingredients combined are critical to the effectiveness of the new composition.

DETAILED DESCRIPTION OF THE INVENTION

The present invention is directed to an attrition and shatter resistant plant nutrient/pesticide briquette composition which slowly releases biologically active materials and plant nutrients to plants in soil. A composition has been discovered which provides these desirable, and heretofore unavailable, properties. The composition comprises slow release plant nutrient particles, having diameters between 0.5 and 5.0 millimeters, amounting to between 50 and 95 percent of the briquette. When the nutrient particles are significantly larger, or smaller, the attrition and shatter resistance of the briquettes are substantially reduced. The same effect is observed when the plant nutrients concentrations are outside of the 50 and 95 percent range.

The effective composition of this invention requires pesticide sorption solids, exhibiting diameters of between 0.5 and 5.0 millimeters and an ability to sorb and reduce leachability of liquid pesticides, amounting to between 2 and 45 percent of the briquette. Some variations in the particle size of the pesticide sorption solids are tolerable, but significant amounts outside the foregoing size range does not provide the desired resistance to attrition and shattering of the briquettes. The pesticide sorption solids must have an ability to absorb, adsorb, or both, liquid pesticides so that the leachability of the liquid pesticides is reduced. This reduction in leachability is usually effected by sorption onto solids with high surface areas, but may also be achieved by dissolution of the liquids into materials on the surface of the solids, or by simple occlusion in the sorption solids. The exact type of sorption may be varied, but it must significantly reduce the leachability of the liquid pesticide applied. The amount of sorption solids may be varied over a substantial range depending upon the type and amount of pesticide employed.

In the instant invention a liquid pesticide, amounting to between 0.1 and 10.0 percent of the pesticide sorption solids, is sorbed on the pesticide sorption solids. Solid pesticides in this system are ineffective and allow unacceptably high leach rates. Amounts of pesticides, less than 0.1 percent provide unacceptably slow release rates from the briquettes and more than 10 percent pesticide concentration provides higher than desirable pesticide release rates and poor briquette resistance to attrition.

The effective composition contains an adhesive, amounting to between 2 and 20 percent of the briquette, which exhibits effective adhesion to both the particles of slow release plant nutrients and the pesticide sorption solids and a low solubility of less than 0.1 gram per 100 grams of water. The adhesive coats the individual particles of the plant nutrients and the pesticide sorption solids. When less than 2 percent adhesive is used attrition and shatter resistance is not effective, and when more than 20 percent is used pesticide release is impaired by the presence of excess adhesive. A water solubility of the adhesive of less than 0.1 gram per 100 grams of water is necessary to prevent rapid degradation of the briquettes in damp soil with earlier than desired release of the pesticide and plant nutrient contained therein.

The adhesive coated particles are formed into briquettes by pressing into dies at pressures and temperatures sufficient to make the briquettes attrition and shatter resistant. The adhesive may be partially cured before the coated particles are pressed into dies with the cure completed in the die as effected by the die pressure and temperature, or the complete cure of the resin may be effected in the die. The shape, or size, of the die is a matter of choice depending upon the desired end use of the briquette. The temperature and pressure used in the die to produce the attrition and shatter resistant briquettes may be arranged depending largely upon the type and amount of adhesive employed, and the speed with which the die is filled, pressed, and discharged.

The composition is particularly effective when the slow release plant nutrient particles have diameters between 0.8 and 2 millimeters and where these particles amount to between 85 and 95 percent of the briquette.

A wide variety of slow release plant nutrient particles may be used in the instant composition and preferred plant nutrients used are magnesium ammonium phosphate, magnesium potassium phosphate, ureaformaldehyde condensates, sulfur, oxamide, isobutylidiene diurea, and crotylidine diurea.

The composition is particularly effective when the pesticide sorption solid particles have diameters between 0.8 and 2.0 millimeters. For effective performance of the composition, the amount of pesticide sorption solids must be controlled within rather narrow limits. Most effective performance is obtained where the pesticide sorption solids amount to between 5 and 10 percent of the briquette.

The preferred pesticide sorption solids are the materials iron humate, wood flour, ground vegetable seed hulls, starch, silica gel, activated carbon, paper waste, and clays.

The amount of liquid pesticide sorbed on the pesticide sorption solids, and thereby contained in the controlled release pesticide and fertilizer briquettes must be maintained at a low level to prevent rapid leaching of the pesticide. Preferred compositions contain liquid pesticide amounting to 0.1 and 5.0 percent of the briquette.

Liquid pesticides may be used directly for sorbing onto the pesticide sorption solids. Where pesticides are normally solid at ambient temperatures, the solid may be dissolved in a liquid solvent and the liquid derived therefrom may be effectively used as a liquid pesticide for sorbing on the pesticide sorption solids.

The type of liquid pesticides used in the new controlled release composition may be selected from any biologically active material which may be put in liquid form and which may be sorbed onto sorption solids and thereby have its leachability significantly reduced. Particularly effective and important biologically active materials for the instant composition are herbicides, insecticides, fungicides, algaecides, acaricides, nematocides, and nitrification inhibitors.

The amount of adhesive required for the composition to be effective is the amount that covers all of the granules in the composition. The adhesive preferably amounts to between 2.5 and 5.0 percent of the briquettes.

A variety of resins may be used as the adhesive with success but the preferred adhesive is one of the following thermoplastic resins: vinylidine chloride, 2-ethylhexyl acrylate, acrylic acid, vinyl acetate, butadiene, natural rubber, and combinations thereof.

A particularly practical and effective composition is obtained when the adhesive, coating the individual particles of the plant nutrients and the pesticide sorption solids, is a thermoplastic resin and the coated particles are formed into briquettes by pressing into dies at a temperature higher than the softening temperature of the thermoplastic resin, and then cooled to a temperature lower than the softening temperature of the thermoplastic resin.

Thermoplastic resins are available commercially as solid, liquids, emulsions, or dispersions. Aqueous emulsions and dispersions are environmentally desirable because they require no organic solvents which must be eventually recovered or lost into the atmosphere. The instant composition is effective where the adhesive coating the individual particles of the plant nutrients and the pesticide sorption solids is a thermoplastic resin, provided as an aqueous dispersion or emulsion which contains between 30 and 70 percent water.

As a practical means of efficient briquette machine operation a die lubricant may be added to the particulate materials to be briquetted. In addition to decreasing damage and wear on the dies, the lubricants usually improve the surface smoothness of the briquettes produced. To provide the desired surface smoothness of briquettes of the present composition, it is preferred that the composition contain a die lubricant amounting to between 0.1 and 0.5 percent of vegetable oils, mineral oils, lignin sulfonate liquids, polyethylene glycols, and polyethylene glycol ethers.

The formation of the instant composition into briquettes may be performed under a variety of conditions depending somewhat on the type and amounts of pesticide sorption solids and the pesticides employed. A preferred composition is obtained where the coated particles are formed into briquettes by pressing into briquette shaped dies at pressures between 1500 and 2500 pounds per square inch at temperatures between 80 and 160° C., and then cooled to a temperature lower than 60° C.

A six step method is the preferred method of preparing attrition and shatter resistant plant nutrient/pesticide briquettes for slow release of plant nutrients and pesticides to plants in soil. The method comprises sizing particles of slow release plant nutrients, amounting to between 50 and 95 percent of the briquettes, so that more than 80 percent of the particles exhibit diameters between 0.5 and 5.0 millimeters.

The particles of pesticide sorption solids are sized so that more than 80 percent of the particles exhibit diameters between 0.5 and 5.0 millimeters and amount to between 2 and 45 percent of the briquettes. The pesticide sorption solids must exhibit an ability to sorb and reduce the leachability of liquid pesticides.

The liquid pesticide, amounting to between 0.1 and 10.0 percent of the briquette is admixed with the pesticide sorption solids until the liquid pesticide is sorbed and the leachability of the liquid pesticide is substantially reduced.

Then, the sized particles of slow release plant nutrient and pesticide sorption solids, containing the sorbed liquid pesticides, are comingled.

The comingled particles of slow release plant nutrients and pesticide sorption particles are coated with an adhesive exhibiting effective adhesion to the particles of slow release plant nutrients and pesticide sorption particles, and a solubility of less than 0.1 gram per 100 grams water. The coating amounts to between 2 and 20 percent of the briquette.

The adhesive coated particles are formed into briquettes by pressing into briquette shaped dies at a pressure between 1500 and 2500 pounds per square inch at a temperature between 80 and 160° C.

The preferred method of preparation is achieved where the adhesive is one of the following thermoplastic resins: vinylidine chloride, 2-ethylhexyl acrylate, acrylic acid, vinyl acetate, butadiene, natural rubber, and combinations thereof.

There are important practical needs for controlled release pesticides and plant nutrient combinations for fertilizing plants growing in soils, while at the same time, protecting the plants from damage from insects, mites, and fungi. Some of the plants which need these treatments are found in ornamental beds and include roses, azaleas, rhododendrons, poinsettias, hydrangeas, and forsythias. These plants are perennials, but are moved, or changed periodically so that it is convenient to fertilize and treat for pests one, or more times per year. The controlled continuous release of plant nutrients and pesticides are useful, and it is desirable to have the pesticides completely released in one year, or less, with about the same release period for the plant nutrients.

Longer release periods for the pesticides are required where seedlings, or small trees, are transplanted from nursery beds for growth to attractive ornamental maturity; or to grow to mature forest trees for harvesting as pulpwood. For healthy growth, these trees require protection against pests, particularly fungi, for periods of at least four years. It is necessary that the pesticides used for the trees need to last for much longer times than those used for the ornamental bed plants.

It is therefore necessary to have a pesticide delivery system in which the pesticide release period may be controlled to meet the need of the particular plants being treated.

1-[(6-chloro-3-pyridinyl)methyl]-N-nitro-2-imidazolidinimine marketed under the tradename MERIT is an insecticide which is effective against white grubs and other insects which destroy ornamentals. It is effective when used as a systemic insecticide. The roots take up the imidachloprid and translocate it throughout the plant so that when the insects ingest part of the plant, the insecticide kills them.

Likewise the fungicide aluminium tris(O-ethyl phosphonate, marketed under the tradename ALIETTE functions as a systemic fungicide. It is used with nursery grown plants to prevent seedling diseases, particularly pythium and root rot. N-2,6-dimethylphenyl)-N-methoxyacetyl)alanine methyl ester, marketed under the tradename of SUBDUE and SUBDUE MAXX, is another systemic fungicide which treats root rot and pythium.

Another effective systemic fungicide 1-(4-chlorophenoxy)-3,3-dimethyl-1-(1H-1,2,4-triazol-1-yl)-2-butanone is marketed under the tradename BAYLETON (Chemical Abstracts No. 43121-43-3). It is particularly effective against fusiform rust, and is readily put in the form of an aqueous dispersion for sorption onto sorptive particles to substantially reduce its leachability, and increase its long term effectiveness when combined as part of the instant briquettes.

When the pure pesticide is a solid material it may not be used per se in the present invention. These pesticides may be effectively used by dissolving them to form solutions, usually in organic solvents. Also, the pesticides in either the finely divided solid, or organic solution form, may be used in the forms of aqueous emulsions or dispersions. The liquid solutions, emulsions, or dispersions are then effectively sorbed onto sorption solids to reduce the leachability of the pesticides. The sorption solids and the controlled release fertilizer granules, may then be appropriately mixed and formed into briquettes.

EXAMPLES OF THE PREFERRED EMBODIMENT

The examples provided here demonstrate the preparation and the utility of the present invention and its preferred embodiment.

Example 1

Particulate potassium ammonium magnesium phosphate, analyzing 7-40-6-13(Mg), with 78.6 percent of the nitrogen and 83.3 percent of the potassium insoluble in cold water, amounting to 900 kilograms was selected as the slow release plant nutrient and was screened so that 94 percent of the particles exhibited diameters between 0.6 and 2.5 mm.

Particulate Bentonite clay, amounting to 100 kilograms, selected as the pesticide sorption solids was screened so that 90 percent of the particles exhibited diameters between 1.0 and 2.4 mm.

Metalaxyl amounting to 1900 grams was converted to a homogeneous aqueous liquid emulsion by high shear mixing with 20 kilograms of water containing 1 percent of mineral oil emulsifier, so that the liquid pesticide amounted to 2% of the total briquette weight.

The metalaxyl emulsion was mixed at ambient temperature with the clay in a closed Littleford high energy mixer until the emulsion was sorbed sufficiently to reduce the leachability of the metalaxyl.

The particulate potassium ammonium magnesium phosphate was blended with the Bentonite based pesticide sorption solids in the Littleford to form a homogeneous mixture. While the mixture was still in the Littleford mixer, 3 percent by weight of DARATAK 3631, a latex containing polyvinylidene chloride, 2-ethylhexyl acrylate, and acrylic acid was sprayed evenly on the homogeneous particle mixture. The coated particles were allowed to cure at ambient temperature for 18 hours.

A mineral oil die lubricant amounting to 0.25 percent was sprayed onto the coated particles as they were fed to a Prater Briquetting Machine, which comprised rollers with opposing half briquette shaped cavities which produced briquettes weighing 7 grams. The particles were augered into the space between the rollers and forced into the briquette-shaped dies (cavities), and there compressed to a pressure of 2500 pounds per square inch. During the compression temperature in the briquettes was increased to 190° F. and the briquettes were discharged from the Prater Machine and cooled to ambient temperature.

The briquettes formed were hard and very resistant to shattering when dropped 30 feet onto a steel plate. Analyses of the briquettes showed the following composition:

| Components | Wt % |
| --- | --- |
| Total N | 6.01 |
| CWIN | 4.75 |
| Total P2O5 | 34.4 |
| Total K2O | 5.3 |
| CWIK | 4.4 |
| Total Mg | 11.2 |
| Metalaxyl content | 1900 parts per million |

Example 2

The efficacy of the product of Example 1 was evaluated in the greenhouse against Pythium fungi in tests where azaleas were grown in small pots. Prior to treatment, all of the soil used in the tests were innoculated with a water suspension of Pythium fungi. The tests were carried out by transferring 10 inch tall azalea plants into 6 inch pots.

A 2-inch layer of soil was placed in the bottom of each pot and a single fertilizer/pesticide briquette was added. The azalea plant was added and the pot was packed with additional soil. The test was evaluated after 6 months. In addition to the treatment with the briquettes from Example 1, pots were treated with: the same material as Example 1, except it contained no metalaxyl, and with no plant nutrients or pesticides. There were three pots for each treatment. The results obtained after 6 months are tabulated as follows:

| Treatment | % of Roots Infected | Plant Appearance |
| --- | --- | --- |
| (1) 6-34-5-11 (Mg) No metalaryl | 89.2 | plants not hardy, less than half the growth of (2) |
| (2) 6-34-5-11 (Mg) Example/products | 2.1 | healthy, good growth |
| (3) Control, no treatment | 94.0 | poor appearance, little growth |

Example 3

Briquettes were made in the same equipment as Example 1 using the same technique, but using magnesium potassium phosphate and ureaformaldehyde condensate powders (36-0-0) combined as the slow release plant nutrients. Ground soybean hulls were the sorption solids; imidachloprid as a 1% aqueous emulsion was the liquid pesticide; and butadiene resin latex was the adhesive to form pesticide/fertilizer briquettes with an analysis as follows:

| Components | Wt % |
| --- | --- |
| Total N | 18.0 |
| CWIN | 8.1 |
| Total P2O5 | 18.0 |
| Total K2O | 6.0 |
| CWIK | 5.3 |
| Total Mg | 6.0 |
| Imidachloprid content | 2000 parts per million |

Example 4

Briquettes were made in the same equipment as Example 1 using the same technique, but using ureaformaldehyde condensate powder (36-0-0), magnesium potassium phosphate, and magnesium ammonium phosphate powders combined as the slow release plant nutrients. Bentonite clay was the sorption solids; BAYLETON as a 1% aqueous emulsion was the liquid pesticide; and DARATAK 3631, a latex containing polyvinylidene chloride, 2-ethyl acrylate and acrylic acid, was the adhesive. The composition of the briquettes produced was as follows:

| Components | Wt % |
|---|---|
| Total N | 7.0 |
| CWIN | 6.1 |
| Total P2O5 | 32.8 |
| Total K2O | 10.1 |
| CWIK | 8.0 |
| Total Mg | 11.2 |
| Bayleton concentration | 1500 ppm |

Example 5

A test was made on Loblolly pine trees in Eastern Virginia sandy soils. Several treatments were made using the briquettes of Example 4. In the tests, pine seedlings were transplanted into holes prepared in the sandy soil. The briquettes were placed in the holes and the seedlings were placed directly above the briquettes. The tests were run with 12 trees used per treatment.

The trees were evaluated, and analyzed after growing periods of 1,2 and 4 years. The trees were examined for fusiform rust and the newest leaves were analyzed for BAYLETON content at each period of evaluation. The results obtained in the tests are tabulated as follows:

| Treatment | BAYLETON in Last Leaf After | | | Percent of Trees Showing Fusarium Rust after 4 years |
|---|---|---|---|---|
| | 1 Year | 2 Years | 4 Years | |
| Control-no treatment | 0 | 0 | 0 | 16 |
| Example 4 Product, except no Bayleton | 0 | 0 | 0 | 24 |
| Example 4 Product, 1500 ppm Bayleton | 1.72ppm | 4.81 | 0.88 | 1 |

At the end of four years the trees of the three treatments had produced positive growth. The trees receiving the fertilizer briquettes with no BAYLETON were about 5 percent larger than the control trees and the trees receiving the fertilizer briquettes containing the BAYLETON were about 10 percent larger than the trees receiving the briquettes without the BAYLETON.

I claim:

1. An attrition and shatter resistant plant nutrient/pesticide briquette composition which slowly releases biologically active materials and plant nutrients to plants in soil, the composition comprises:

(a) slow release plant nutrient particles, exhibiting diameters of between 0.5 and 5.0 millimeters, amounting to between 50 and 95 percent of the briquette;

(b) pesticide sorption particles, exhibiting diameters of between 0.5 and 5.0 millimeters and an ability to sorb and reduce leachability of liquid pesticides, amounting to between 2 and 45 percent of the briquette;

(c) liquid pesticide amounting to between 0.1 and 10.0 percent of the pesticide sorption solids sorbed on the pesticide sorption solids;

(d) an adhesive, amounting to between 2 and 20 percent of the briquette, exhibiting effective adhesion to the particles of slow release plant nutrients and the pesticide sorption solids, and a solubility of less than 0.1 gram per 100 grams of water, the adhesive coating the particles of the plant nutrients and the pesticide sorption solids; and, (e) the adhesive coated particles being formed into briquettes by pressing into dies at a pressure and temperature sufficient to make the briquettes attrition and shatter resistant.

2. The composition of claim 1 wherein the slow release plant nutrient particles exhibit diameters between 0.8 and 2 millimeters.

3. The composition of claim 1 wherein the slow release plant nutrient particles amount to between 85 and 95 percent of the briquette.

4. The composition of claim 1 wherein the slow release plant nutrient particles are selected from the group of slow release plant nutrients consisting of: magnesium ammonium phosphate, magnesium potassium phosphate, ureaformaldehyde condensates, sulfur, oxamide, isobutylidiene diurea, and crotylidine diurea.

5. The composition of claim 1 wherein the pesticide sorption solids particles exhibit diameters between 0.8 and 2.0 millimeters.

6. The composition of claim 1 wherein the pesticide sorption solids amount to between 5 and 10 percent of the briquette.

7. The composition of claim 1 wherein the pesticide sorption solids are selected from the group of sorptive materials consisting of iron humate, wood flour, ground vegetable seed hulls, starch, silica gel, activated carbon, paper waste, and clays.

8. The composition of claim 1 wherein the liquid pesticide amounts to between 0.1 and 5.0 percent of the briquette.

9. The composition of claim 1 wherein the liquid pesticide comprises a solid pesticide dissolved in a liquid solvent.

10. The composition of claim 1 wherein the liquid pesticide is selected from the group of biologically active materials consisting of herbicides, insecticides, fungicides, algaecides, acaricides, nematocides, and nitrification inhibitors.

11. The composition of claim 1 wherein the liquid pesticide is selected from the group of systemic pesticides consisting of 1-[(6-chloro-3-pyridinyl)methyl]-N-nitro-2-imidazolidinimine, aluminum tris (O-ethyl phosphonate), N-(2,6-dimethylphenyl)-N-(methoxyacetyl)alanine methyl ester, and 1-(4-chlorophenoxy)-3,3-dimethyl-1-(1H-1,2,4-triazol-1-yl)-2-butanone.

12. The composition of claim 1 wherein the adhesive amounts to between 2.5 and 5.0 percent of the briquette.

13. The composition of claim 1 wherein the adhesive is selected from the group of thermoplastic resins consisting of vinylidene chloride, 2-ethylhexyl acrylate, acrylic acid, vinyl acetate, butadiene, natural rubber and combinations thereof.

14. The composition of claim 1 wherein the adhesive coating the particles of the plant nutrients and the pesticide sorption solids is a thermoplastic resin and the coated particles are formed into briquettes by pressing into dies at a temperature higher than the softening temperature of the thermoplastic resin, and cooled to a temperature lower than the softening temperature of the thermoplastic resin.

15. The composition of claim 1 wherein the adhesive coating the particles of the plant nutrients and the pesticide sorption solids is a thermoplastic resin, provided as an aqueous dispersion or emulsion containing between 30 and 70 percent water.

16. The composition of claim 1, additionally containing a die lubricant amounting to between 0.1 and 0.5 percent, selected from the group consisting of vegetable oils, mineral oils, lignin sulfonate solutions, polyethylene glycols, and polyethylene glycol ethers.

17. The composition of claim 1 wherein the coated particles are formed into briquettes by pressing into briquette shaped dies at pressure between 1500 and 2500 pounds per square inch at temperatures between 80 and 160° C., and then cooled to a temperature lower than 60° C.

18. A six step method of preparing attrition and shatter resistant plant nutrient/pesticide briquettes for slow release of plant nutrients and pesticides to plants in soil, the method comprising:

(a) sizing particles of slow release plant nutrients, amounting to between 50 and 95 percent of the briquettes, so that more than 80 percent of the particles exhibit diameters between 0.5 and 5.0 millimeters;

(b) sizing particles of pesticide sorption solids amounting to between 2 and 45 percent of the briquettes and exhibiting an ability to sorb and reduce leachability of liquid pesticides, so that more than 80 percent of the particles exhibit diameters between 0.5 and 5.0 millimeters;

(c) admixing liquid pesticide, amounting to between 0.1 and 10.0 percent of the briquette, with the pesticide sorption solids until the liquid pesticide is sorbed so that the leachability of the liquid pesticide is substantially reduced;

(d) comingling the sized particles of slow release plant nutrients and pesticide sorption solids containing the sorbed liquid pesticides;

(e) coating the comingled particles with an adhesive, exhibiting effective adhesion to particles of slow release plant nutrients and pesticide sorption particles and a solubility of less than 0.1 gram per 100 grams of water, amounting to between 2 and 20 percent of the briquette; and, (f) forming the adhesive coated particles into briquettes by pressing into briquette shaped dies at a pressure between 1500 and 2500 pounds per square inch at a temperature between 80 and 160° C.

19. The method of claim 18 wherein the adhesive is a thermoplastic resin selected from the group consisting of vinylidene chloride, 2-ethylhexyl acrylate, acrylic acid, vinyl acetate, butadiene, natural rubber, and combinations thereof.

* * * * *